United States Patent
Henedi

(10) Patent No.: US 8,895,262 B1
(45) Date of Patent: Nov. 25, 2014

(54) STAINING METHOD FOR IDENTIFICATION OF FLATWORMS

(71) Applicant: Adawia A. M. Henedi, Khitan (KW)

(72) Inventor: Adawia A. M. Henedi, Khitan (KW)

( * ) Notice: Subject to any disclaimer, the term of this patent is extended or adjusted under 35 U.S.C. 154(b) by 0 days.

(21) Appl. No.: 14/302,007

(22) Filed: Jun. 11, 2014

(51) Int. Cl.
*G01N 1/30* (2006.01)

(52) U.S. Cl.
CPC ............................. *G01N 1/30* (2013.01)
USPC .......................................... 435/40.5

(58) Field of Classification Search
CPC ........................................... G01N 1/30
USPC ........................................... 435/40.5
See application file for complete search history.

(56) References Cited

U.S. PATENT DOCUMENTS 6,387,708 B2    5/2002    Wardlaw

OTHER PUBLICATIONS

Henedi and El-Azazy, A simple technique for staining of platyhelminths with the lactophenol cotton blue stain. Journal of the Egyptian Society of Parasitology, vol. 43, No. 2 (Aug. 2013). pp. 419-423.*

"Evaluation of Lacto-Phenol Cotton Blue for Wet Mount Preparation of Feces," *Journal of Clinical Microbiology*, Apr. 1995, 1019-1021, Parija and Prabhakar.

A.A. Henedi and C.M. El-Azazy, "A simple technique for staining of platyhelminths with the lactophenol cotton blue stain", J. Egypt Soc. Parasitol., 43(2), Aug. 2013, pp. 419-423, Abstract only.

* cited by examiner

*Primary Examiner* — Jon P Weber
*Assistant Examiner* — Kara Johnson
(74) *Attorney, Agent, or Firm* — Richard C Litman

(57) ABSTRACT

The staining method for identification of flatworms includes placing a sample flatworm specimen on a microscope slide, mounting the flatworm specimen on the slide with a small amount of lactophenol cotton blue (LPCB) stain, waiting two to three minutes for the stain to be absorbed by flatworm tissues, covering the specimen with a cover slip, and examining the stained specimen with a microscope to identify the species-distinctive organs of the flatworm. For permanent mounting, the cover slip may be sealed to the microscope slide by nail polish. The method is effective for trematodes (flukes) and cestodes (tapeworms). Before examination, the specimen may be preserved by obtaining the flatworm from a carrier or host, washing the flatworm in saline and preserving the flatworm in alcohol, e.g. 70% alcohol.

14 Claims, No Drawings

STAINING METHOD FOR IDENTIFICATION OF FLATWORMS

BACKGROUND OF THE INVENTION

1. Field of the Invention

The present invention relates to laboratory methods for identifying helminth parasites found in human and animal organs, particularly to a staining method for identification of flatworms by microscopic examination.

2. Description of the Related Art

Parasitic flatworms, including cestodes (tapeworms) and digeneans (flukes), can cause different diseases in animals and humans. Species specific identification of the parasitic flatworm is typically important in diagnosing a particular disease of a carrier. Different anatomical structures or organs of adult flatworms are particularly useful in identifying a particular flatworm species. Differentiation of the two human *Taenia* species *Taenia saginata* and *Taenia solium* (pork tapeworm), for example, is based on the number of uterine branches or on the absence or presence of hooks in the scolex of the tapeworm. Distinguishing between the two types of worms is important because *Taenia saginata* is relatively innocuous, whereas infection with *Taenia solium* (pork tapeworm) has major health effects due to extra-intestinal infection by the larval or cyst phase in the central nervous system. Thus, prompt identification of a particular tapeworm species in a carrier may be important for diagnosing, treating, and/or preventing infections.

Current staining methods for identifying flatworms are often time-consuming, require several steps, involve many chemicals, and must be conducted by a skilled technician. Therefore, a simplified procedure for staining flatworms is desirable.

Thus, a staining method for identification of flatworms solving the aforementioned problems is desired.

SUMMARY OF THE INVENTION

The staining method for identification of flatworms includes placing a sample flatworm specimen on a microscope slide, mounting the flatworm specimen on the slide with a small amount of lactophenol cotton blue (LPCB) stain, waiting two to three minutes for the stain to be absorbed by flatworm tissues, covering the specimen with a cover slip, and examining the stained specimen with a microscope to identify the species-distinctive organs of the flatworm. For permanent mounting, the cover slip may be sealed to the microscope slide by nail polish. The method is effective for trematodes (flukes) and cestodes (tapeworms). Before examination, the specimen may be preserved by obtaining the flatworm from a carrier or host, washing the flatworm in saline and preserving the flatworm in alcohol, e.g. 70% alcohol. The LPCB stain may selectively stain parts or organs of the flatworm to facilitate visualization of the various parts or organs of the flatworm with a microscope.

These and other features of the present invention will become readily apparent upon further review of the following specification.

DETAILED DESCRIPTION OF THE PREFERRED EMBODIMENTS

The staining method for identification of flatworms includes placing a sample flatworm specimen on a microscope slide, mounting the flatworm specimen on the slide with a small amount of lactophenol cotton blue (LPCB) stain, waiting two to three minutes for the stain to be absorbed by flatworm tissues, covering the specimen with a cover slip, and examining the stained specimen with a microscope to identify the species-distinctive organs of the flatworm. For permanent mounting, the cover slip may be sealed to the microscope slide by nail polish. The method is effective for trematodes (flukes) and cestodes (tapeworms). The particular species of the flatworm may be determined based on the visible parts or organs of the flatworm.

The sample including the flatworm may be preserved for examination by obtaining the flatworm from a carrier or host of the flatworm, washing the flatworm in saline and preserving the flatworm in alcohol, e.g. 70% alcohol. Optionally, the flatworm may be cut into numerous segments and/or flattened, as is known in the art, prior to fixing in the alcohol. The sample including the flatworm may include one or more separated segments or parts of the flatworm, e.g., the proglottids and/or scolex. The sample including the flatworm may include a whole flatworm, or more than one flatworm. The flatworm may be an adult flatworm. The flatworm may be a parasitic flatworm. The flatworm may be a fluke or a tapeworm.

Once the sample is prepared, the sample may then be contacted with the LPCB stain. The sample may be contacted with the LPCB stain in any suitable manner. For example, the LPCB stain may be applied to a microscope slide and the sample may be immersed therein to allow the flatworm to absorb the LPCB stain. The sample may be positioned on a microscope slide and the LPCB stain may be applied thereon to allow absorption of the LPCB stain into the flatworm.

It is preferred that a minor amount of the LPCB stain be used that will still provide a visible differentiation between the selected organs or parts of the flatworm. In other words, the LPCB stain may be in an amount sufficient to define or distinguish anatomical parts, including internal organs of the flatworm, when the sample is examined with a microscope. Determination of the amount of LPCB stain to be used will depend upon the size of the worm or worm section to be examined. A cover slip may be used to cover the sample. For permanent preparations, nail polish or other suitable lacquer may be applied to edges of the cover slip to affix the cover slip to the slide. Preferably, the sample is immersed in the LPCB for about two to three minutes prior to covering the sample with the cover slip. The stained sample may be visualized by a microscope, for example, a light microscope at a magnification of ×40 and/or ×100.

The LPCB stain creates a satisfactory level of staining of the flatworm to facilitate visualization of the parts or organs of the flatworm. With the LPCB stain, mesenchymal tissue adjacent internal organs of the flatworm may not be stained to a substantial extent, or at least to a significantly lesser extent than the internal organs. Accordingly, when the sample is visualized with a microscope, the parts or organs of the flatworm may be clearly distinguishable from adjacent tissue. For example, use of the LPCB stain may facilitate visualization of the suckers, pharynx, intestinal caecum, testes, ootype, vitelline duct, vitellaria, ovary, uterus, cirrus sac, seminal vesicle, vas deferens, cirrus, taenioid shaped hooks, rose thorn shaped hooks, rostellum, and/or eggs of the flatworm.

It should be understood that the carrier may be a human or animal carrier or host of the parasitic flatworm. The flatworm may be retrieved from the carrier in any suitable manner known in the art.

Lactophenol cotton blue (LPCB) is a well-known stain composed of phenol, lactic acid, glycerol, and methyl blue dye. LPCB preparations are commercially available from many laboratory suppliers. LPCB has been used for the identification of various fungal infections, but its use for identification of flatworms has not been previously reported.

The following examples illustrate the method.

EXAMPLE 1

Heterophyes heterophyes

Adults of *Heterophyes heterophyes*, a trematode species, were removed from the small intestine of stray cats. The adult flatworms were washed in saline and preserved in 70% alcohol and placed on a clean slide. An amount of the LPCB stain (obtained from MERCK (Germany)) was placed on the trematode. The worm specimen was immersed in the LPCB mountant/stain. After two to three minutes, the specimen was covered with a cover slip. Nail polish was applied to edges of the cover slip. The specimen was then examined with a microscope at a magnification of ×40 and ×100. The LPCB stain differentiated the oral sucker, pharynx, genital sucker, ovary, vitellaria, ventral sucker, testis, seminal vesicle, and uterus from adjacent tissue, thereby allowing visualization of these worm parts. The testes and ovary could be seen situated in a posterior part of the worm. The gonads were stained light blue. The vitelline glands were stained deep blue, occupying the posterior lateral field of the worm. The ventral sucker could be seen in the middle of the worm body, and appeared twice larger than the oral sucker. Both the ventral sucker and the oral sucker were deeply stained. The genital sucker appeared postero-lateral to the ventral sucker. The genital sucker was deeply stained and about 77 rodlet spines could be seen.

EXAMPLE 2

Mesostephanus dottrensi

Adults of *Mesostephanus dottrensi*, a trematode species, were removed from the small intestine of stray cats. The adult flatworms were washed in saline and preserved in 70% alcohol. The worm specimen was placed on a clean microscope slide. An amount of the LPCB stain (obtained from MERCK (Germany)) was placed on the worm. The worm specimen was immersed in the LPCB mountant/stain. After two to three minutes, the specimen was covered with a cover slip. Nail polish was applied to edges of the cover slip. The specimen was then examined with a microscope at a magnification of ×40 and ×100. The LPCB stain differentiated the oral sucker, pharynx, intestinal caecum, vitellaria, ovary, testis, cirrus sac, seminal vesicle, and ventral sucker from adjacent tissue, thereby allowing visualization of these worm parts. The testes appeared large, ovoid, tandem in position and situated in the posterior half of the body. The ovary appeared nearly pyramidal in shape and lay postero-lateral to the anterior testis. The gonads were stained light blue. The subterminal oral sucker and pharynx were well-developed and deeply stained, whereas the acetabulum was lightly stained and lay in the middle of the worm body. The vitelline glands were well-developed, appeared as deeply stained, irregularly shaped and closely packed follicles, confined in horse-shoe manner around the gonads. The cirrus sac, in the postero-lateral region of the body, was deeply stained, and contained the seminal vesicle and rod shaped cirrus.

EXAMPLE 3

Diplopylidium species (strobila)

Adults of *Diplopylidium* species, a cestode species, were removed from the small intestine of stray cats. The adult flatworms were washed in saline. The strobila of the flatworm was cut into small parts, each part including several segments, flattened and fixed in 70% alcohol and stretched on a clean microscope slide. An amount of the LPCB stain obtained from MERCK (Germany) was placed on the strobila. After two to three minutes, the specimen was covered with a cover slip. Nail polish was applied to edges of the cover slip. The specimen was then examined with a microscope at a magnification of ×40 and ×100. The LPCB stain differentiated the vagina, seminal receptacle, ovary, vitellaria, vas deferens, cirrus sac, cirrus, and testis from adjacent tissue, thereby allowing visualization of these worm parts. The mature *Diplopylidium* segment included two sets of genital organs. The ovary appeared bilobed in shape and the two compact lobes were separated by the deeply stained seminal receptacle. The vitelline gland was situated posterior to the ovary. The vagina extended across the cirrus pouch and opened anterior to the male genital opening. Numerous testes could be visualized. The testes were round and situated in the middle field of the segment. The convoluted vasa deferens were deeply stained and situated in the upper part of the segment. The cirrus pouch was sacular, containing the deeply stained cirrus.

EXAMPLE 4

Diplopylidium species (scolex)

Adults of *Diplopylidium* species, a cestode species, were removed from the small intestine of stray cats. The adult flatworms were washed in saline. The scolex of the flatworm was separated from the flatworm and fixed in 70% alcohol and placed on a clean microscope slide. An amount of the LPCB stain obtained from MERCK (Germany) was placed on the scolex. The scolex was immersed in the LPCB mountant/stain. After two to three minutes, the specimen was covered with a cover slip. Nail polish was applied to edges of the cover slip. The specimen was then examined with a microscope at a magnification of ×40 and ×100. The LPCB stain differentiated the taenioid shaped hooks, rose thorn shaped hooks, rostellum, and sucker from adjacent tissue, thereby allowing visualization of these worm parts. It could be seen that the flatworm included four suckers and rostellum which had four alternating rows of deeply stained hooks. It could be seen that the first three rows included taenioid shaped hooks and the last row included small rose-thorn shaped hooks.

It is to be understood that the present invention is not limited to the embodiments described above, but encompasses any and all embodiments within the scope of the following claims.

I claim:

1. A staining method for identification of flatworms, comprising the steps of:
   placing a sample flatworm specimen on a microscope slide;
   mounting the flatworm specimen on the slide with lactophenol cotton blue (LPCB) stain;
   waiting two to three minutes for the stain to be absorbed by flatworm tissues;
   covering the specimen with a cover slip; and
   examining the stained specimen with a microscope to identify species-distinctive organs of the flatworm.

2. The staining method according to claim 1, further comprising the steps of:
   obtaining the flatworm specimen from an organ of a human being or animal;
   washing the flatworm specimen; and
   preserving the flatworm in alcohol.

3. The staining method according to claim 2, further comprising the step of cutting the flatworm specimen.

4. The staining method according to claim 2, further comprising the step of flattening the flatworm specimen.

5. The staining method according to claim 1, wherein the sample flatworm specimen includes at least one part of the flatworm.

6. The staining method according to claim 5, wherein the sample flatworm specimen includes a proglottid.

7. The staining method according to claim 5, wherein the sample flatworm specimen includes a scolex.

8. The staining method according to claim 1, wherein the sample flatworm specimen includes a whole flatworm.

9. The staining method according to claim 1, wherein the sample flatworm specimen includes a plurality of whole flatworms.

10. The staining method according to claim 1, wherein the sample flatworm specimen is an adult flatworm.

11. The staining method according to claim 1, wherein the sample flatworm specimen is a parasitic flatworm.

12. The staining method according to claim 1, wherein the sample flatworm specimen is a trematode (fluke).

13. The staining method according to claim 1, wherein the sample flatworm specimen is a cestode (tapeworm).

14. The staining method according to claim 1, further comprising the step of sealing the cover slip to the microscope slide with nail polish.

\* \* \* \* \*